United States Patent [19]  
Intille

[11] 4,067,900  
[45] Jan. 10, 1978

[54] HYDROGENOLYSIS OF ALCOHOLS, KETONES, ALDEHYDES, ESTERS AND ETHERS

[75] Inventor: George M. Intille, Maryland Heights, Mo.

[73] Assignee: Monsanto Company, St. Louis, Mo.

[21] Appl. No.: 607,308

[22] Filed: Aug. 25, 1975

[51] Int. Cl.$^2$ ............................................. C07C 67/08
[52] U.S. Cl. ................................... 560/138; 260/690; 260/613 R
[58] Field of Search ........................... 260/690, 479 R

[56] References Cited

U.S. PATENT DOCUMENTS

| | | | |
|---|---|---|---|
| 3,428,661 | 2/1969 | Taylor | 260/690 |
| 3,489,786 | 1/1970 | Dewhirst | 260/690 |
| 3,759,838 | 9/1973 | Dewhirst | 260/690 |

*Primary Examiner*—Paul J. Killos  
*Attorney, Agent, or Firm*—Joseph D. Kennedy; John D. Upham

[57] ABSTRACT

The present invention relates to a process for the preparation of saturated hydrocarbons from alcohols, ketones, aldehydes, esters or ethers by hydrogenolysis in the presence of catalyst systems containing an iridium or rhodium component and a halogen component. The process is specifically directed to the production of methane from methanol, toluene from benzaldehyde, ethyl benzene from methyl benzyl alcohol or acetophenone, bis(p-hydroxyphenyl) ethane from anisoin.

29 Claims, No Drawings

HYDROGENOLYSIS OF ALCOHOLS, KETONES, ALDEHYDES, ESTERS AND ETHERS

This invention relates to a process for preparation of saturated hydrocarbons or derivatives thereof by hydrogenolysis of alcohols, ketones, aldehydes, esters, or ethers or derivatives thereof. It represents an efficient and selective way of removing an alcohol, ketone, aldehyde, ester or ether function from an organic molecule. More particularly, it relates to a process for the reaction of alcohols, ketones, aldehydes, esters or ethers in the presence of a catalyst system having an iridium or rhodium component and a halogen component, preferably iodine, to yield the corresponding saturated molecule in which the alcohol, ketone, aldehyde, ester or ether function has been removed selectively and efficiently. Moreover more than one of such functions can be removed at the same time if more than one is present.

BACKGROUND OF THE INVENTION

Hydrogenolysis of oxygen functions such as alcohols, ketones, aldehydes, esters, or ethers has been known in the art. The prior art teaches a number of catalysts for this reaction among them being copper chromite, $CuO.CuCr_2O_8$ and palladium or carbon. These suffer from several disadvantages. Severe conditions of temperature and pressure are required, typically temperatures greater than 250° C and pressures in excess of 3000 psi are required. In addition the reactions under these conditions are usually very non-selective and other unwanted side reactions occur. Furthermore only certain types of alcohols are hydrogenolyzed even under the most severe conditions employed. Primary alochols such as methanol for instance are resistant to hydrogenolysis even under the most severe reaction conditions. These systems also suffer from the tendency to be susceptible to poisoning from trace substituents such as sulfur.

Reduction of oxygen functions, stoichiometrically by expensive reducing agents such as $LiAlH_4.AlCl_3$ or Sn and HCl are also known but are not particularly useful due to the expense of the reducing agent which is used up in the reaction.

It is therefore the object of this invention to overcome the above disadvantages and thus provide an improved and more economically and commercially feasible hydrogenolysis process in which molecular hydrogen is used to form saturated compounds from alcohols, ketones, aldehydes, esters, or ethers.

Another object of this invention is to provide a more reactive and more stable catalytic hydrogenolysis system than has heretofore been described in the prior art, and one which will readily convert even primary alcohols to saturated hydrocarbon.

Still another object of the present invention is to provide a more selective and more reactive catalytic hydrogenolysis system for the removal of oxygen functionality from organic compounds.

Still another object is to provide a procedure for converting alkyl phenol ethers to phenols and alkanes.

Still another object of the present invention is to provide an improved hydrogenolysis process enabling the efficient and selective production of such useful materials as methane from methanol or bis (paramethoxy-phenyl) ethane from anisoin in the presence of an improved and more stable catalyst system, thus enabling the use of lower temperature and lower pressure than has generally been possible heretofore and facilitating product isolation, catalyst recovery and recycle without substantial catalyst decomposition and loss.

These and other objects of the present invention will become apparent to those skilled in the art from the accompanying description of the invention.

SUMMARY OF THE INVENTION

In accordance with the present invention a feed comprising an alcohol, ketone, aldehyde, ester, or ether is converted selectively to the corresponding saturated product in which the oxygen function has been removed, by reacting the feed component in the liquid or vapor phase with hydrogen, preferably at temperatures from about 50° C to 300° C and at partial pressures of hydrogen from 1 psig to 15,000 psig. This is accomplished in the presence of a catalyst system containing as active constituents an iridium or rhodium component, preferably iridium, and a halogen component, preferably iodide. The present process is particularly advantageous at lower pressures although higher pressures may also be used. The hydrogen is generally used in sufficient excess over other gaseous components to obtain a high yield of the saturated compound.

DESCRIPTION OF THE PREFERRED EMBODIMENTS

As referred to above for the purposes of the present invention the catalyst system essentially includes an iridium or rhodium component and a halogen component. Generally, the iridium or rhodium component of the catalyst system of the present invention is believed to be present in the form of a coordination compound of iridium or rhodium with a halogen component providing at least one of the ligands of such coordination compound. In addition to the iridium or rhodium and halogen in the process of the present invention these coordination compounds also generally include carbon monoxide ligands or hydride ligands thereby forming such compounds or complexes of iridium or rhodium as $Ir(CO)_3Br$, $Ir(CO)_2I_2^-$, $Ir(CO)_2Br_2^-$, $[Ir(CO)_4I_2]^-$, $[Ir(CO)I_4]_2^{2-}$, $HIr(CO)_2I_2$, $[RH(CO)_2Br]_2$, $[Rh(CO)_2I]_2$ and the like. Other moities may be present if desired. Generally it is preferred that the catalyst system contain as a promoting component an excess of halogen over that present as ligands in the iridium or rhodium coordination compounds. The terms "coordination compound" and "coordination complex" used throughout this specification means a compound or complex formed by combination of one or more electronically rich molecules or atoms capable of independent existence with one or more electronically poor molecules or atoms each of which may also be capable of independent existence.

The essential iridium or rhodium and halogen component of the catalyst system of the present invention may be provided by introducing into the reaction zone a coordination compound of iridium or rhodium containing halogen ligands or may be provided by introducing into the reaction zone separately an iridium or rhodium component and a halogen compound. Among the materials which may be charged to the reaction zone to provide the iridium or rhodium component of the catalyst system of the present invention are iridium or rhodium metal, iridium or rhodium salts and oxides, organo iridium or rhodium compounds, coordination compounds and the like. Specific examples of materials capable of providing the iridium or rhodium constituent of the catalyst system of the present invention may be taken from the following non-limiting partial list of suitable materials.

$IrCl_3$
$IrBr_3$
$IrI_3$
$IrCl_3 \cdot 4H_2O$
$IrBr_3 \cdot 4H_2O$
$Ir(CO)_2Cl_2$ salts
$Ir(CO)_2Br_2$ salts
$Ir(CO)_2I_2$ salts
$[(n-C_4H_9)_4N][Ir(CO)_2X_2]$ where $X = Br^{31}, I^-$
$[(n-C_4H_9)_4As]_2[Ir_2(CO)_4Y_4]$ where $Y = Br^-$ or $I$
$[(n-C_4H_9)_4P][Ir(CO)I_4]$
$Ir[(C_6H_5)_3P]_2(CO)Br$
$Ir](n-C_4H_9)_3P]_2(CO)Br$
$Ir[(n-C_4H_9)_2P]_2(CO)I$
$IrBr[(C_6H_5)_3P]_3$
$Ir_2(CO)_8$
$Ir[(C_6H_5)_3P]_2(CO)I$
$Ir[(C_6H_5)_3P]_2(CO)Cl$
$IrCl[(C_6H_5)_3P]_2(CH_3I)(CO)$
$Ir(SnCl_3)[(C_6H_5)_3P]_3$
Ir metal
$Ir(NO_3)_3$
$IrCl(CO)[(C_6H_5)_3As]_2$
$IrI(CO)[(C_6H_5)_3Sb]_2$
$IrCl[(C_6H_5)_3P]_3$
$IrCl[(C_6H_5)_3P]_3H_2$
$[(C_6H_5)_3P]_3Ir(CO)H$
$[Ir(C_2H_4)_2Cl]_2$
$K_4Ir_2Cl_2(SnCl_3)_4$
$Ir_2O_3$
$K_4Ir_2Br_2(SnBr_3)_4$
$K_4Ir_2I_2(SnI_3)_4$
$IrO_2$
$RhCl_3$
$RhBr_3$
$RhI_3$
$RhCl_3 \cdot 3H_2O$
$RhBr_3 \cdot 3H_2O$
$Ph_2(CO)_4Cl_2$
$Rh_2(CO)_4Br_2$
$Rh_2(CO)_4I_2$
$Rh_2(CO)_8$
$Rh[(C_6H_5)_3P]_2(CO)I$
$[(n-C_4H_9)_4N][Rh(CO)_2X_2]$ where $X = Cl^-, Br^-, I^-$
$[(n-C_4H_9)_4As]_2[Rh_2(CO)_2Y_4]$ where $Y = Br^-, I^-$
$[(n-C_4H_9)_4P][Rh(CO)I_4]$
$Rh[(C_6H_5)_3P]_2(CO)Br$
$Rh[(n-C_4H_9)_3P]_2(CO)Br$
$Rh[(n-C_4H_9)_3P]_2(CO)I$
$RhBr[(C_6H_5)_3P]_3$
$RhI[(C_6H_5)_3P]_3$
$RhCl[(C_6H_5)_3P]_3$
$RhCl[(C_6H_5)_3P]_3H_2$
$Rh[(C_6H_5)_3P]_2(CO)Cl$
Rh metal
$Rh(NO_3)_3$
$Rh[(C_6H_5)_3P]_2(CH_3)I_2$
$Rh(SnCl_3)[(C_6H_5)_3P]_3$
$RhCl(CO)[(C_6H_5)_3As]_2$
$RhI(CO)[(C_6H_5)_3Sb]_2$
$[(C_6H_5)P]_3Rh(CO)H$
$RH_2O_3$
$[Rh(C_2H_4)_3Cl]_2$
$K_4Rh_2Cl_2(SnCl_3)_4$
$K_4Rh_2Br_2(SnBr_3)_4$
$K_4Rh_2I_2(SnI_3)_4$ With the above materials capable of providing the iridium or rhodium component but not containing a halogen component it will be necessary to introduce into the reaction zone such a halogen component. For example if the iridium or rhodium component is introduced as iridium metal, rhodium metal, $IrO_2$ or $Rh_2O_3$ it will be necessary to introduce a halide component such as methyl iodide, hydrogen iodide, iodine or the like.

As noted above, while the halogen component of the catalyst system may be in combined form with the iridium or rhodium as for instance, one or more ligands in a coordination compound of iridium or rhodium, it generally is preferred to have an excess of halogen present in the catalyst system as a promoting component. By excess is meant an amount of halogen greater than two atoms of halogen per atom of iridium or rhodium in the catalyst system. This promoting component of the catalyst system consists of halogen and/or halogen compound such as hydrogen halide, alkyl- or aryl halide, metal halide, ammonium halide, phosphonium halide, arsonium halide, stibonium halide and the like. The halogen of the promoting components may be the same or different from that already present as ligands in the coordination compound of iridium or rhodium. Generally the halogen in the promoting component is iodine, bromine, or chlorine with iodine and bromine being preferred and iodine being the most preferred. Accordingly suitable halogen containing or promoting components may be selected from the following list of halogen and/or halogen containing compounds.

| | | |
|---|---|---|
| R—X | where R = any alkyl or aryl group, and X = Cl, Br, I | e.g. $CH_3I$, $C_6H_5Br$, $CH_3CH_2I$, etc. |
| $X_2$ or $X_3^-$ | where X = Cl, Br, I | e.g. $Cl_2$, $I_2$, $I_3^-$ |
| HX | where X = Cl, Br, I | e.g. HBr, HI |
| RCX ‖ O | where R = aryl, alkyl or aryl group and X = Cl, Br, I | e.g. $CH_3CI$ etc. ‖ O |
| $M_yX_z$ | where M = any metal and y = 1–20 and z = 1–20 and X = Cl, Br, I | e.g. LiI, NaBr etc. |
| $R_4MX$, $R_4MX_3$, $R_2MX_2$ | where R = H or any alkyl or aryl group, and M = N, P, As, Sb and X = Cl, Br, I | e.g. $H_4NI$, $PH_4I_3$, $R_3PBr_2$, etc. |

Although any amount of the promoting component of the catalyst system of the present invention may be employed, the amount employed is usually such as to produce a ratio of atoms of halogen to atoms of iridium or rhodium in the catalyst system of from 2:1 to 50,000:1 and higher. However the preferred ratio is from 2:1 to 5,000:1. A more preferred ratio is 3:1 to 1000:1, and usually at least 20:1.

Preferably, the process of the present invention is carried out in an acidic reaction medium. For purposes of the present invention an acidic reaction medium is defined as one in which an alkyl or acyl halide is present or will be formed. The alkyl or acyl halide usually is one in which the alkyl radical or acyl radical corresponds to an alkyl or acyl radical of the feed alcohol, ester, ether, ketone, or aldehyde.

Such alkyl or acyl halides may be added to the reaction medium as such or may be formed in situ within the reaction medium from the feed alcohol, ester, ether, aldehyde, or ketone and the halide present in the catalyst system. The reaction medium is considered acidic when under reaction conditions as herein set forth at least 0.01% of the total halogen atoms present in the system are present as the alkyl halide or acyl halide. Preferably at least 1.0% of the total halogen atoms in the system are present as the alkyl or acyl halide.

The liquid reaction medium employed may include any solvent compatible with the catalyst system such as alcohols, esters, ethers, aldehydes, or ketones, mixtures of alcohol, ester, ether, aldehydes and ketones feedstocks and/or carboxylic acids or esters. The preferred solvent and liquid reaction medium for the present invention is carboxylic acids. Water may also be present or added to the reaction mixture if desired.

Suitable feedstocks include alcohols of general formula R—OH, where R is a hydrocarbyl radical of, for example, 1–50 carbon atoms. R may be an alkyl such as methyl, ethyl, neopentyl etc. It may also be a cycloalkyl such as cyclohexyl, cyclooctyl, etc. The carbon directly attached to the OH group cannot be part of an aromatic ring but aromatic rings may be included elsewhere in the hydrocarbyl chain, i.e. aryl or other substituted carbinols can be used. Thus phenol is not a suitable feedstock but benzyl alcohol is. Thus alcohol is used in its usual sense as a compound with a hydroxyl group on aliphatic carbon. In addition the hydrocarbyl chain may have hetero atoms included in it as well. If the hetero atoms include oxygen and if the oxygen group is of the proper type i.e. alcohol, ketone, aldehyde, ester or ether it may also be hydrogenolyzed. Thus ethylene glycol is a suitable substrate and will form ethane. Various other non-interfering substituents can be included on the hydroxyl group.

Another suitable feedstock is a ketone of general formula

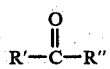

where R' and R" are defined the same as R above, including substituents, except that R' and R" can be aromatic.

Another feedstock is an aldehyde of general formula

where R' is defined as above.

Another feedstock is an ether of general formula R—O—R'. At least one of R or R' must have non-aromatic carbon attached to the oxygen, and otherwise are defined as R above. If R is non-aromatic and R' is aromatic such as in anisole, only the non-aromatic side of the ether will be hydrogenolyzed. Thus anisole will yield methane and phenol. If both R and R' are non-aromatic both sides will be hydrogenolyzed. Thus bibenzyl ether will yield two moles of toluene.

Another feedstock is an ester of formula

where R has non-aromatic carbon attached to the oxygen and otherwise R and R' are defined as above, i.e. the ester is that of an alcohol and a carboxylic acid.

The hydrocarbyl or other moieties on the oxy function can also contain non-aromatic unsaturation such as carbon-to-carbon double or triple bonds, although such groups may well be hydrogenated in the reaction which of course is acceptable if saturated products are desired. Various primary, secondary or tertiary alcohols can be used, and the class of oxy, oxo, and oxa alkanes is generally suitable, e.g. alkoxy-, aryloxy, acyloxy-, keto- and aldehydo-alkanes. Such non-interfering substituents as halides can be present on the hydrocarbyl moieties, and some such groups may be replaced by hydrogen in the reaction which can at times be a desirable result. In other cases, substituents will not be affected and the process will be useful for selective replacement of oxygen functions by hydrogen.

In accordance with the present invention the hydrogenolysis reaction may be carried out by intimately contacting the above defined feed component which, depending on the carbon number and operating conditions, may either be in the vapor or liquid phase, with gaseous $H_2$ in a liquid phase containing a catalyst system having an iridium component and a halogen containing promoting component such as HI and LiI under conditions of temperature and pressure suitable as described herein to form the hydrogenolysis product. The particular conditions selected are the same whether the feed component is charged as a vapor or liquid. The temperature will accordingly generally be in the range of 50° C to 300° C with the preferred range being 100° C to 240° C. Partial pressures of hydrogen of the order of 1 psig to 15,000 psig may be employed, however 5 psig to 3000 psig hydrogen partial pressure is generally preferred and a more preferred range is from 10 psig to 1000 psig. Higher pressures may be used if desired under appropriate conditions.

Alternatively hydrogenolyzed products may be produced is desired via reaction of the feed components and $H_2$ in the vapor phase over the iridium or rhodium containing catalyst system described above, dispersed upon solid supports. Such a catalyst system may be operated as a conventional fixed bed reactor. For example, methanol, methyl iodide, and $H_2$ may be passed over a catalyst system such as $Ir(CO)_3I_3$ dispersed on a solid support material such as Alundum, activated carbon, clays, alumina, silica-alumina, ceramics, etc. in a fixed bed reactor maintained at elevated temperatures and pressures to produce methane in high yields. However the use of a liquid reaction medium as above described is preferred in the process of this invention.

While any amount of $H_2$ may be employed, a typical hydrogenolysis reaction requires at least one and in some cases two moles of $H_2$ per mole of alcohol, ester, ether, aldehyde or ketone. Excess of $H_2$ over the stoichiometric amount however may be present. Hydrogen streams containing inert impurities such as CO, $CO_2$, $CH_4$, $N_2$ noble gases, water and paraffinic hydrocarbons, may be employed if desired for example from available plant gas streams with no adverse effect. The concentration of $H_2$ in the feed gas mixture is from 1 vol.% to 100 vol.%, a preferred range being from 10 vol.% to 99 vol. %.

The reaction rate is dependent on catalyst concentration and temperature. Concentrations of the iridium or rhodium containing component of the catalyst system in the liquid phase between $10^{-6}$ moles/liter and $10^{-1}$ moles/liter are normally employed with the preferred range being $10^{-4}$ moles/liter to $10^{-2}$ moles/liter. However higher concentration even to the extent of more than 1 mole/liter may be used if desired. Higher temperatures also favor higher reaction rates.

It has been found that water may exert an effect on the reaction. Water is also produced in the reaction. Water may be added in addition to that produced to effect the rate of the reaction. For example amounts of water to constitute up to about one-third of the liquid volume may be added. The ionic strength of the iodide in solution also has an effect on the reaction rate but a wide range of ionic strengths are permissible.

The reaction is also best carried out in the presence of a small amount of gaseous CO. It is believed that the most active form of the catalyst is one containing between 1 and 6 CO ligands per metal. The amount of CO gas may vary over a wide range; however, at least one mole of CO per mole of metal is preferred and it may be present in even greater amounts. If a large excess of CO is present a competing reaction, carbonylation of the alcohol to form carboxylic acids becomes important. Therefore in order to avoid this reaction an excess of CO is to be avoided when hydrogenolysis is the desired reaction, and hydrogen should be in excess of other gaseous components. The preferred concentration of CO in the gas phase in from 1–10%, and it should be less than 20% of the hydrogen on a molar basis. It is convenient to employ carbon monoxide partial pressures no greater than about 2 Kgm/cm². In carrying out the above described embodiment for the production of hydrogenolyzed products the purification system employs a distillation train to recover the products by distillation while the remaining higher boiling components which contain the components of the catalyst system are recycled.

In the absence of other compounds as solvents having a higher boiling point than the products (discussed below) a portion of the reaction solution containing the iridium or rhodium and halogen catalyst system is recycled to the reactor to return said catalyst system to the reaction zone.

The active iridium or rhodium containing catalyst system is preferably supplied as a catalyst solution. The solution can also contain liquid reactants, products, and mixtures thereof (such as recycle streams) which function as solvents for the reaction media.

The above catalyst solutions essentially comprised of (1) the reactant feed component-product medium, (2) an iridium or rhodium component, and (3) a halogen component generally in molar excess of the iridium or rhodium as hereinabove set forth, may be further modified by the addition of an inert solvent as a further component. Inert solvents which are suitable include paraffinic hydrocarbons of from 4–50 carbon atoms, aromatic hydrocarbons of from 6 to 40 carbon atoms, organic acids of from 2 to 20 carbon atoms and esters composed of the aforesaid acids in combination with the feedstock undergoing hydrogenolysis, and also orthophosphorous and orthosilicon alkoxy esters, as well as chlorine, bromine, and iodine containing derivatives of all of the above said solvents. The following list exemplifies such solvents: dodecane, hexadecane, naphthalene, biphenyl, propionic acid, octanoic acid, phthalic anhydride, benzoic acid, dioctyl phthalate, dimethyl phthalate, ethyl benzoate, triphenyl phosphate, tetramehthyl orthosilicate, chloronaphthalene, chlorinated biphenyls, etc.

The most preferred group of inert solvents from the above are the carboxylic acids of from 2 to 20 carbon atoms such as acetic acid, propionic acid, benzoic acid, octanoic Acid, etc.

The inert solvents as described above refer to the actual molecular species which are present in the hydrogenolysis reaction mixture. Consequently modified derivatives may be charged initially, for example an ester having a number of carbon atoms which is greater or less than the aforesaid ranges by one or two or more carbon atoms. Under reaction conditions in the presence of the feedstock (i.e. alcohol for instance) such esters undergo ester interchange to equilibrium species which are within the above ranges, and it will be further understood that the ranges are only intended as approximate guides. Another embodiment of the process utilizes a high-boiling inert solvent. Such an inert solvent must have a boiling point at least 25° C higher (S.T.P.) than the product and/or feed. An example of such a high boiling inert solvent is dimethyl phthalate. Such an inert solvent along with the feed (for example methanol) together with the active iridium or rhodium component (for example $Ir(CO_2I_2^-)$) and the halogen component comprises the liquid reaction medium. In this embodiment, particularly suited for use with gas-sparged reactor systems the feed is a liquid or gas and is introduced along with gaseous hydrogen. The product stream is then removed as a vapor containing for instance methane. In this embodiment of the invention, no liquid is withdrawn so that a distinct advantage exists because of the elimination of catalyst handling and consequently a minimization of catalyst losses. The vapor stream leaving the reactor can be purified separately by standard techniques into product streams and unreacted feed which can be recycled.

Another embodiment of the present invention comprises performing the hydrogenolysis in a carboxylic acid solvent containing the feedstock, the iridium or rhodium component, and the halogen promoter. Since many of the feedstocks (for instance benzyl alcohol) are miscible with this solvent system the critical reaction solution starts out as one phase. The hydrogenolysis products (for example toluene and water) are no longer miscible with the solvent resulting in a two phase system.

Also separation into two phases can be caused by addition of excess water at the end of the reaction. In this embodiment the separation of the hydrogenolyzed product is facilitated by the phasing out of the reaction solution. This embodiment is particularly useful when complex, high boiling, or unstable products or reactants are used such as, in the formation of bis-(p-phenol) ethane from anisoin. The product which would be difficult to remove by distillation is separated quite easily when acetic acid is used as an inert solvent by simply adding water at the end of the reaction and separating the product from the non-aqueous phase.

In order to provide for a better understanding of the process of the present invention as disclosed and claimed herein, a number of specific embodiments of the process are presented below. The examples presented below are not to be construed as in any manner limiting to the scope of the invention.

EXAMPLE 1

A batch reactor is charged with the following ingredients: 0.19g $IrCl_3$, 1.33g LiI, 2.7 cc 47% aqueous HI, 4 cc $H_2O$, 70 cc propionic acid as solvent and 30 cc methyl benzyl alcohol as feedstock. The reactor is pressurized to a total pressure of 58 kgm/cm² of which the partial pressure of CO is about 21 Kgm/cm² and partial pressure of $H_2$ is 35 Kgm/cm². The reaction vessel is heated to 185° C and hydrogen gas is added as needed to maintain a constant pressure. After 20 hours the temperature is lowered and the products analyzed by gas chromatography. The methyl benzyl alcohol was quantitatively converted to ethyl benzene along with some carboxylation product, 2 phenyl propionic acid. Other forms of iridium and iodine give similar results.

EXAMPLE 2

A reaction as in Example 1 was conducted in which the CO pressure was about 2 Kg/cm² and the hydrogen partial pressure was 71 Kgm/cm², and hydrogen was added to maintain such pressure. The solvent was acetic acid and the reaction temperature, 195° C. The methyl benzyl alcohol was quantitatively converted to ethyl benzene. No other products were detectable by gas chromatographic analysis.

EXAMPLE 3

A reaction as in Example 2 was conducted in which the solvent was acetic acid and the feedstock was anisoin. The products were identified as a mixture of compounds of formula $(-CH_2.\Phi-OX)_2$ where X = H or Me or Ac or mixtures thereof along with methane in the gas phase. These products can be accounted for by the following reactions, although other reactions may be involved:

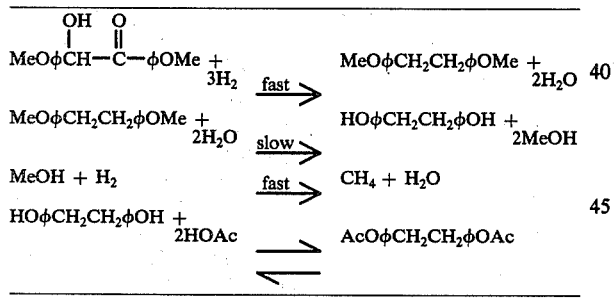

The results illustrate three points about the invention.
1. the aliphatic alcohol and ketone are quantitatively reduced,
2. the aromatic half of the ether is not hydrogenolyzed, and
3. the methyl half of the ether can be converted to methane.

The product can be directed toward the free phenol or the acylated derivative by raising or lowering the amount of water in the acetic acid medium. In addition, short reaction time as by removal of product can be utilized to influence the reaction toward the bis(methoxyphenyl) ethane.

EXAMPLE 4

A reaction as in Example 3 was performed and a rate of 1.7 product/liter/hr was observed. After the reaction water was added and two phases separated. The aqueous phase contained the acetic acid solvent and the components of the catalyst. The organic phase contained the same product as in Example 3.

EXAMPLE 5

A reaction as in Example 3 was performed using acetic anhydride as the solvent. The reaction was slower but essentially the same products were formed.

EXAMPLE 6

A reaction as in Example 2 was performed where the feedstock was benzaldehyde. The feed was quantitatively converted with 90% yield of toluene and 10% of bibenzyl.

EXAMPLE 7

A reaction as in Example 2 was performed when the $IrCl_3$ was replaced by $RhCl_3$. The reaction was slower but about 10% of the methyl benzyl alcohol was converted to ethyl benzene. The remaining unhydrogenolyzed alcohol was esterified under reaction conditions to the acetate ester.

EXAMPLE 8

A reaction as in Example 2 was performed where LiBr and HBr replaced the LiI and HI. The reaction was again slower than Example 2 but the products were the same as in Example 7.

EXAMPLE 9

A reaction as in Example 2 was performed in which the feedstock was methanol. The methanol was quantitatively converted to methane. The conversion rate for the first hour of reaction was 3 moles/liter/hour. One of the advantages of the present invention is the relatively mild conditions which can be utilized for hydrogenolysis of primary alcohols, for example hydrogen pressures no greater than about 140 Kgm/cm², and temperatures no greater than about 240° C, with even much milder pressures and temperatures being suitable for methanol and other primary alkanols.

EXAMPLE 10

A reaction as in Example 2 was performed in which the feedstock was methyl acetate. The products were methane and acetic acid and conversion was quantitative.

EXAMPLE 11

A reaction as in Example 2 where the feedstock was butyl ether. The product was butane.

EXAMPLE 12

Benzyl alcohol was reacted in accordance with the procedure of Example 2 to obtain quantitative conversion to toluene. The rate for the first hour was 2.7 moles/liter/hour.

EXAMPLE 13

Ethanol was reacted in accordance with the procedure of Example 2 to obtain 70% conversion to ethane, with the remaining ethanol being esterified to ethyl acetate. In the same procedure, isopropyl alcohol gave 60% conversion to propane, and tertiary butyl alcohol was converted quantitatively to 2-methyl propane.

EXAMPLE 14

Acetophenone was reacted in accordance with the procedure of Example 2 to obtain quantitative conversion to ethylbenzene, with a rate of 1.5 moles/liter/hour in the first hour of reaction. In the same procedure acetone was quantitatively converted to propane, at a rate of 0.4 mole/liter/hour.

EXAMPLE 15

A reaction like that of Example 3 was effected utilizing anisoin as reactant. The conversion was 70%, with yields (on initial anisoin) of 35% bisphenol ethane, 35% bisphenol ethane acetate derivative and 70% methane. The conversion rate was 2 moles/liter/hour in the first hour.

EXAMPLE 16

Methanol was hydrogenolyzed in accordance with the procedure of Example 2, but employing a hydrogen partial pressure of about 7 Kgm/cm² and adding hydrogen to maintain such pressure. The methanol was converted to methane at a rate of 0.3 mole/liter/hour.

One particularly significant application of the present invention is its use in converting anisoin to a bis (phenol) ethane or derivative thereof, as anisoin is an available material for such reaction, and the fact that the keto and alcohol groups are hydrogenolyzed, but the phenol groups are present in the product, provides a convenient route to a useful product. The bis-phenol ethane is a monomer useful for preparing polyester resins, as by interpolymerization with isophthalic acid.

What is claimed is:

1. A process for the hydrogenolysis of alcohols, ethers having oxygen attached to aliphatic carbon, ketones, aldehydes and carboxylic esters which comprises contacting at least one of such compounds with hydrogen and a catalyst having as essential an iridium or rhodium component and a halogen component, in which halogen is selected from the group consisting of iodine, bromine, and chlorine, in amount sufficient to catalyze the hydrogenolysis and with the hydrogen being present in sufficient excess over other gaseous components to cause hydrogenolysis in which oxygen cleaved from a carbon atom in the said compounds is replaced by hydrogen under conditions to obtain a high yield and recovery of products of such hydrogenolysis.

2. The process of claim 1 in which the catalyst includes an iridium component.

3. The process of claim 2 in which the catalyst includes an iodine component.

4. The process of claim 2 in which the process is carried out in the presence of water, HI and Li.

5. The process of claim 1 in which the contacting is effected at temperatures of 50° to 300° C and a hydrogen gauge pressure of 1 to 15,000 psi.

6. The process of claim 1 in which the reaction is effected in atmosphere consisting essentially of hydrogen.

7. The process of claim 1 in which a small amount of carbon monoxide, constituting less than 20% on a molar basis of the hydrogen is present.

8. The process of claim 1 in which a small amount of carbon monoxide is present but at a partial pressure no greater than about 2 Kgm/cm².

9. The process of claim 1 in which the process is carrier out in aqueous carboxylic acid medium.

10. The process of claim 2 in which the halogen to iridium atomic ratio is in the range of 2:1 to 50,000:1.

11. The process of claim 2 in which the halogen to iridium atomic ratio is at least 20:1.

12. The process of claim 1 in which a primary alkanol is converted to an alkane.

13. The process of claim 12 in which hydrogen pressures no greater than about 140 Kgm/cm² are utilized.

14. The process of claim 1 in which methanol is converted to methane.

15. The process of claim 2 in which the catalyst is dispersed on an inert solid support.

16. The process of claim 2 in which the reaction is carried out in the vapor phase.

17. A process for hydrogenolysis of ethers having oxygen attached to aliphatic carbon, aldehydes and ketones which comprises contacting at least one of such compounds with a catalyst having as essentials an iridium or rhodium component and a halogen component, in which halogen is selected from the group consisting of iodine, bromine and chlorine, in amount sufficient to cause hydrogenolysis in which oxygen cleaved from a carbon atom is replaced by hydrogen under conditions to obtain a high yield and recovery of products of such hydrogenolysis.

18. The process of claim 17 in which a

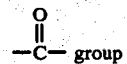

is converted to a

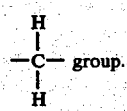

19. The process of claim 17 in which a phenolic ether, ROR', in which R is an organic moiety with the oxygen attached to aliphatic carbon and R' is an organic moiety with the oxygen attached to aromatic carbon, is converted to RH and a phenol, R'OH or an ester thereof.

20. The process of claim 17 in which an alkyl ether of a phenol is converted to an alkane and a phenol.

21. The process of claim 17 in which anisoin is the compound utilized and keto and alcohol groups therein are hydrogenolyzed to obtsin a bis (oxyphenyl) ethane.

22. The process of claim 21 in which the product consists of at least one of bisphenol ethane and carboxylic acid ester derivatives thereof.

23. The process of claim 5 in which the catalyst includes an iridium component and the halogen to iridium ratio is at least 20:1 and CO is present at less than 20% on a molar basis of the hydrogen.

24. The process of claim 23 in which the reaction is carried out in an acidic reaction medium.

25. The process of claim 24 in which the process is carried out in aqueous carboxylic acid medium.

26. The process of claim 25 in which a ketone is hydrogenolyzed.

27. The process of claim 17 in which anisoin is hydrogenolyzed to a bis (oxyphenyl) ethane.

28. The process of claim 17 in which a ketone is hydrogenolyzed.

29. The process of claim 25 in which the catalyst includes an iodine component.

* * * * *